US009743868B2

(12) United States Patent
Ballam et al.

(10) Patent No.: US 9,743,868 B2
(45) Date of Patent: Aug. 29, 2017

(54) CIRCUITRY TO ALLOW LOW CURRENT OPERATION OF A DEVICE CAPABLE OF DETERMINING A BLOOD PROPERTY

(71) Applicant: QUALCOMM Incorporated, San Diego, CA (US)

(72) Inventors: Robert Scott Ballam, Eatons Hill (AU); Robert Bruce Ganton, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 161 days.

(21) Appl. No.: 14/549,167

(22) Filed: Nov. 20, 2014

(65) Prior Publication Data
US 2016/0143566 A1 May 26, 2016

(51) Int. Cl.
*A61B 5/1455* (2006.01)
*A61B 5/00* (2006.01)
(Continued)

(52) U.S. Cl.
CPC ...... *A61B 5/14552* (2013.01); *A61B 5/02427* (2013.01); *A61B 5/02438* (2013.01);
(Continued)

(58) Field of Classification Search
CPC ............ A61B 5/14551; A61B 5/02416; A61B 5/14552; A61B 5/7207; A61B 5/4818
See application file for complete search history.

(56) References Cited

U.S. PATENT DOCUMENTS 6,226,539 B1 * 5/2001 Potratz ............... A61B 5/14551
356/41
6,226,639 B1 5/2001 Lindsay et al.
(Continued)

FOREIGN PATENT DOCUMENTS

EP 1722673 A1 11/2006
EP 1722673 B1 4/2009
(Continued)

OTHER PUBLICATIONS

Tavakoli et al., "An Ultra-Low-Power Pulse Oximeter Implemented With an Energy-Efficient Transimpedance Amplifier," IEEE Transactions on Biomedical Circuits and Systems, Institute of Electrical and Electronics Engineers, Feb. 2010, vol. 4(1), pp. 27-38, URL: < http://hdl.handle.net/1721.1/62185 >.
(Continued)

*Primary Examiner* — Eric Winakur
*Assistant Examiner* — Marjan Fardanesh
(74) *Attorney, Agent, or Firm* — The Marbury Law Group

(57) ABSTRACT

Systems, methods, and devices of the various embodiments provide a device capable of determining a blood property based at least in part on the measurement of the amount of light received by a receiver circuit with a limited current capacity by charging a capacitor with a low voltage power supply and intermittently discharging the capacitor through a light emitting diode. In some embodiments the device may be a pulse oximeter capable of taking blood oxygen readings. In some embodiments the device may be a heart rate monitor to determine a heart rate based on an amount of light passed through tissue. The various embodiments may enable pulse oximeters and/or heart rate monitors to be incorporated into small unobtrusive body patches, while enabling
(Continued)

the pulse oximeters to operate from a power output equivalent to that of a small coin cell battery or printed cell battery.

24 Claims, 10 Drawing Sheets

(51) Int. Cl.
*A61B 5/024* (2006.01)
*A61B 5/026* (2006.01)

(52) U.S. Cl.
CPC .......... *A61B 5/6826* (2013.01); *A61B 5/7278* (2013.01); *A61B 5/7292* (2013.01); *A61B 5/0261* (2013.01); *A61B 5/6816* (2013.01); *A61B 5/7239* (2013.01); *A61B 2560/0204* (2013.01); *A61B 2560/0214* (2013.01); *A61B 2560/0412* (2013.01); *A61B 2562/0238* (2013.01); *A61B 2562/164* (2013.01)

(56) References Cited

U.S. PATENT DOCUMENTS

| | | | |
|---|---|---|---|
| 7,499,740 B2 | 3/2009 | Nordstrom et al. | |
| 8,560,036 B2 | 10/2013 | Baker, Jr. | |
| 8,571,622 B2 | 10/2013 | Huiku et al. | |
| 2003/0163054 A1* | 8/2003 | Dekker | A61B 5/02416 600/502 |
| 2005/0187453 A1 | 8/2005 | Petersen et al. | |
| 2007/0088207 A1* | 4/2007 | Mannheimer | A61B 5/14551 600/323 |
| 2007/0120542 A1 | 5/2007 | LeMay | |
| 2008/0198964 A1* | 8/2008 | VanMetter | A61B 6/541 378/8 |
| 2009/0247849 A1 | 10/2009 | McCutcheon et al. | |
| 2013/0035735 A1* | 2/2013 | Kroll | A61N 1/3962 607/4 |
| 2013/0060098 A1* | 3/2013 | Thomsen | A61B 5/02028 600/301 |
| 2013/0137938 A1* | 5/2013 | Peters | A61B 5/0205 600/301 |
| 2013/0324855 A1* | 12/2013 | Lisogurski | A61B 5/0205 600/476 |
| 2015/0257663 A1 | 9/2015 | Deliwala | |
| 2015/0289791 A1 | 10/2015 | Marcus | |

FOREIGN PATENT DOCUMENTS

| | | |
|---|---|---|
| WO | 03024325 A2 | 3/2003 |
| WO | 2005082237 A1 | 9/2005 |

OTHER PUBLICATIONS

Partial International Search Report—PCT/US2015/060273—ISA/EPO—dated Feb. 25, 2016.
International Search Report and Written Opinion—PCT/US2015/060273—ISA/EPO—dated Jul. 11, 2016.

* cited by examiner

CIRCUITRY TO ALLOW LOW CURRENT OPERATION OF A DEVICE CAPABLE OF DETERMINING A BLOOD PROPERTY

BACKGROUND

Continuous monitoring of vital signs with the ability to remotely monitor patient status is a growing field and the ability to incorporate multiple measurement capabilities into a single small unobtrusive patch that can be worn by a patient (i.e., a body worn patch) for multiple days at a time is a desirable feature. One such measurement is blood oxygen concentration, often carried out by a pulse oximeter. However, current pulse oximeter designs are not conducive to being powered by an ultra-low power source, such as a small coin cell battery, and thus not suited for incorporation into a body worn patch.

SUMMARY

The systems, methods, and devices of the various aspects provide a device capable of determining a blood property based at least in part on the measurement of the amount of light received by the receiver circuit, such as taking blood oxygen and/or pulse readings, while being powered by a power source with a limited current capacity. The various aspects may enable a device, such as a pulse oximeter or heart monitor, to be incorporated into a small unobtrusive body patch, while enabling the device to be powered by a current source equivalent to that of a small coin cell battery or printed cell battery. In an example device, a small coin cell battery or printed cell battery may be used to charge a capacitor. When the capacitor reaches a predefined voltage, the battery/charging circuit may be disconnected from the capacitor, and electricity may be allowed to flow from the capacitor to a light-emitting diode (LED). Because the LED no longer needs to be driven by a constant current, this technique may eliminate the need for a constant current and/or high power source in the device. In some example systems, methods, and devices the device may be a heart rate monitor capable of taking heart rate measurements while being powered by a power source with a limited current capacity. In some example systems, methods, and devices the device may be a pulse oximeter monitor capable of taking blood oxygen measurements while being powered by a power source with a limited current capacity.

In an example device, a photodetector may be closely synchronized with the discharge of the capacitor through the LED. An output of a photodetector may be connected to an integrating capacitor. Just before the charging capacitor is connected to the LED to cause the LED to switch on, the integrating capacitor may be discharged. When the LED is switched on, a portion of the photons emitted by the LED may be detected by the photodetector, which may convert these detected photons to a current that is integrated (i.e., stored) by the integrating capacitor. As the LED is switched off, a microprocessor of the device may measure the voltage stored in the integrating capacitor to determine the output of the photodetector, which may be converted to an LED signal amplitude or used to calculate blood oxygen concentration. Minimizing the time between discharging the integrating capacitor and turning on the LED and also the time between turning off the LED and taking a voltage reading of the integrating capacitor may minimize the amount of ambient light detected by the circuit and improve overall performance of the circuit.

In an aspect, current demand may be further limited by timing when measurements are taken to coincide with desired points in a patient's pulse cycle in order to minimize the amount of time that the circuit is energized to take samples. To synchronize with the pulse cycle, multiple preliminary samples may be taken with the LED over a short amount of time, such as one second. These samples may be frequent enough to span a complete pulse cycle regardless of the patient's current heart rate. In another aspect, the samples may be taken such that a full set of readings is not taken over one pulse cycle. Taking samples over less than the complete pulse cycle may increase the time required to obtain an initial reading, while reducing the current draw on a coin cell battery or printed cell battery. Using measurements from the preliminary sample, the microprocessor of the device may calculate the patient's heart rate and timing by observing changes in measurement values. The processor may use the calculated values to anticipate subsequent pulse maxima and minima and activate the circuitry to take readings at those points in the pulse cycle or waveform. A minimal number of readings may then be taken on each subsequent pulse cycle or waveform. For example, readings may be limited such that just enough readings are taken to ensure that readings remain synchronized to the maxima and minima portions of the pulse waveform. If the patient's pulse rate changes, the microprocessor may adjust the predicting timing of pulse maxima and minima to follow. If necessary, the processor may resynchronize with the heart rate by taking a full second's worth of samples and use those samples to recalculate the timing of pulse maxima and minima.

BRIEF DESCRIPTION OF THE DRAWINGS

The accompanying drawings, which are incorporated herein and constitute part of this specification, illustrate exemplary embodiments of the teachings of the disclosure, and together with the general description given above and the detailed description given below, serve to explain the features of the disclosure.

DETAILED DESCRIPTION

Figure 1:
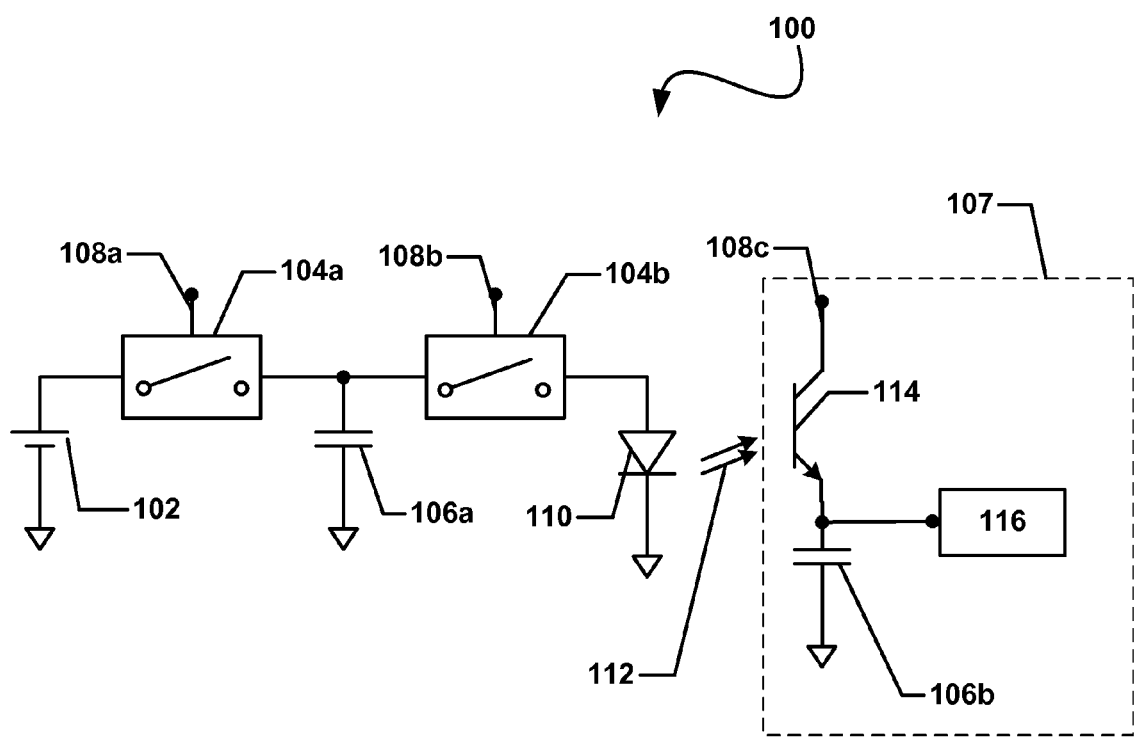
FIG. 1 is a circuit diagram illustrating first embodiment circuit for device, such as a pulse oximeter or heart rate monitor, configured to minimize current draw.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

Pulse oximeters monitor oxygen levels in the blood stream. Pulse oximeters typically operate by shining light of two different wavelengths through a body part and measuring the relative differences in the amplitude of the original light and the received light at the two different wavelengths. For example, one wavelength may be red and the other infrared. Blood with lower levels of oxygen may tend to absorb less infrared light and more red light. Alternatively, blood with higher levels of oxygen may tend to absorb more infrared light and less red light. Thus, a properly calibrated pulse oximeter may determine oxygen levels by emitting light of red and infrared wavelengths and measuring the relative amounts of red and infrared light after the light has passed through a body part, such as a fingertip or earlobe.

Pulse oximeters require a power source to provide current to the sources of light (e.g., light-emitting diodes or LEDs). One solution is to continuously provide power to LEDs such that they are always on and the pulse oximeter constantly collects data. One example design is a pulse oximeter that uses a high precision current sink to control LEDs that are driven with a voltage-controlled source. These current pulse oximeter designs generally consume a considerable amount of boost power. However, lower power sources that may not be capable of providing continuous power sufficient to power the LEDs of a pulse oximeter may be cheaper and more efficient than high power sources, and may therefore be preferable for use in pulse oximeters. Moreover, continuously providing power to LEDs may not be well suited for incorporation into a body worn patch because high current consumption requires larger batteries that are not compatible with the patch form factor. For instance, typical LED drive current levels are approximately 10 mA, whereas typical coin cell batteries are limited to a maximum current draw of approximately 6 mA.

The various embodiments include a device, which may be a pulse oximeter or heart rate monitor, capable of operating based upon low voltage and/or current power sources, such as coin cell batteries or printed cell batteries. Coin cell batteries or printed cell batteries may be low current power sources that cannot supply high continuous current. For example in comparison to Lithium ion batteries that may supply 0.5 current continuous (i.e., 0.5 times the batteries rated capacity, such that a 70 mA battery may supply 35 mA for two hours), coin cells may only supply relatively small currents for a short duration (typically around 6 mA for a few seconds). The systems, methods, and devices of the various embodiments provide a heart rate monitor capable of taking heart rate measurements while being powered by a power source with a limited current capacity, such as coin cell batteries or printed cell batteries.

The systems, methods, and devices of the various embodiments include device, such as a pulse oximeter capable of taking blood oxygen readings or a heart rate monitory capable of monitoring heart beats, with the measurements being taken while drawing limited current. The various embodiments may enable devices (e.g., pulse oximeters) to be incorporated into small unobtrusive body patches, while enabling the devices to operate within the voltage and current constraints equivalent to that of a small coin cell battery or printed cell battery. In an embodiment pulse oximeter, a small coin cell battery or printed cell battery may charge a capacitor (sometimes referred to herein as the "charging capacitor"). When the charging capacitor reaches a predefined voltage it may be disconnected from the battery/charging circuitry (e.g., via a switch), and connected (e.g., via a switch) to the LED so that the stored charge may flow from the capacitor through an LED causing it to illuminate briefly. The charging capacitor may be disconnected from the battery/charging circuitry before being connected to the LED. To measure the oxygen concentration, light transmitted through the patient's tissues may be measured by using a photodetector to convert photons into current. In an embodiment, the output of the photodetector may be accumulated or integrated over the duration of the LED illumination using a second capacitor (sometimes referred to herein as the "integrating capacitor"). Thus, the illuminating LED is activated periodically using power stored in the charging capacitor and measurements are taken simultaneously using a photodetector coupled to an integrating capacitor. Because the LED no longer needs to be driven by a constant current, this technique may eliminate the need for a constant current and/or high power source in the pulse oximeter. Also, the periodic operation reduces the amount of power drawn from the battery, extending the operating life of the circuit when powered by a battery. Additionally, drawing a lower current over longer time increases the power efficiency of many batteries, further helping to make a coin cell battery or printed cell battery a viable power source for the pulse oximeter.

In an embodiment pulse oximeter, measurements of light by the photodetector may also be closely synchronized with the flash of the LED, and thus with the connection of the charging capacitor to the LED. For example, the photodetector may be connected to the integrating capacitor to begin the integration of its output signal just before the LED fires. The photodetector may then disconnect from the integrating capacitor to cease integration just after the LED turns off. A microprocessor of the pulse oximeter may control the actuation of switches that connect the charging capacitor to the LED and connect the integrating capacitor to the photodetector. The microprocessor may measure the output of the photodetector by measuring the voltage of the integrating capacitor. In an embodiment, the voltage of the integrating capacitor may be converted to LED signal amplitude. Limiting the time in which the photodetector measures an input may minimize ambient light detection, resulting in more accurate measurements.

In an embodiment, the current drawn by the pulse oximeter may be further limited by minimizing the measurements that are taken. This may be achieved by synchronizing measurements to the patient's pulse cycle (also referred to as the pulse waveform), and only taking measurements at particular points of interest, such as at the point of maximum blood flow ("pulse maxima") and at the point of minimum blood flow ("pulse minima"). To achieve such synchronization the processor of the pulse oximeter may perform a synchronization routine in which multiple preliminary samples are taken over a short period of time, such as one second. The short period of time, such as one second, may be a length of time selected to increase the likelihood that at least one full pulse cycle will occur while the multiple preliminary samples are being taken. The samples may be taken frequently enough to provide adequate resolution of the pulse cycles regardless of the patient's heart rate. The microprocessor of the pulse oximeter may use the measurements gathered in the preliminary samples to calculate the heart rate and detect the timing of the pulse maxima. Using this information the processor may anticipate when subsequent maxima and minima will occur and schedule measurements accordingly. A minimal number of readings may then be used for each subsequent pulse(s), such as readings taken just at the pulse maxima and pulse minima. Readings may be limited so that just enough readings are taken to ensure that the processor can adjust the timing of readings so they remain synchronized to the pulse maxima and minima. If synchronization is lost, the microprocessor may resynchronize with the heart rate, such as by taking a full second's worth of samples and recalculate the anticipated maxima and minima.

In an embodiment, synchronization may be performed without taking a full set of readings over one pulse cycle. The microprocessor of the pulse oximeter may initially subsample the waveform and adjust the timing until it has locked onto the pulse waveform. In comparison to taking a full set of readings over one pulse cycle, this type of synchronization may take longer to obtain an initial reading. However, synchronization without taking a full set of readings over one pulse cycle may provide the advantage of drawing less peak power from the low current power source, such as a coin cell battery or printed cell battery. In an embodiment, a few readings, such as two or more readings, may be taken close together to enable the slope of the waveform to be observed and heart rate to be estimated. The timing of measurements may then be adjusted to lock onto the maxima and minima of the pulse or heartbeat cycles/waveforms.

Low voltage power sources alone may not be capable of continuously providing sufficient current to standard light sources, such as LEDs. The various embodiments address this characteristic of low voltage power sources with a pulse oximeter in which the light source(s) is powered by a capacitor that is charged by the power source. The capacitor may be coupled to the light source to emit light (and the pulse oximeter may gather data) intermittently. By avoiding a constant drain on the low voltage power source, the embodiment pulse oximeters may operate solely based upon a low voltage power source, such as a coin cell battery or printed cell battery.

FIG. 1 is a circuit diagram illustrating an embodiment circuit 100 for a device (e.g., a pulse oximeter or heart rate monitor) configured to minimize current draw of the circuit 100. In an embodiment, the circuit 100 may be integrated into an electronic patch worn by a patient. A low voltage source 102, such as a coin cell battery or printed cell battery, may be connected to a charging capacitor 106a by a voltage control element 104a. The voltage control element 104a may control when the low voltage source 102 charges the charging capacitor 106a. Persons skilled in the art will appreciate that the voltage control element 104a may be any type of controllable component capable of alternately electrically isolating the charging capacitor 106a from the low voltage source 102 and electrically connecting the charging capacitor 106a to the low voltage source 102. For instance, the voltage control element 104a may be a switch, a voltage regulator, a field effect transistor (FET), a switch mode power supply (SMPS), etc. Preferably, the voltage control element 104a may be capable of electrically isolating the charging capacitor 106a such that when the LED 110 is turned on no further charge leaks onto the charging capacitor 106a from the low voltage source 102.

The charging capacitor 106a may also be connected to a LED 110 by a voltage control element 104b. The voltage control element 104b may be any type of controllable component capable of alternately electrically isolating the charging capacitor 106a from the LED 110 and electrically connecting the charging capacitor 106a to the LED 110, such as a transistor, field effect transistor (FET), switch, etc.

In an embodiment, the low voltage source 102 may supply a constant voltage. For a sufficiently constant voltage supply, there may be no need for a voltage regulator on the capacitor. However, the voltage supplied by some voltage sources, such as batteries, may diminish over time. To compensate for a changing voltage output by the low voltage source 102, it may be desirable to measure the voltage on the charging capacitor 106a or utilize a regulator (e.g., a low dropout regulator or a boost regulator) to charge the capacitor to a constant voltage independent of the changing voltage output of the voltage source 102. The voltage control element 104a may be controlled via a microprocessor to vary the amount of charge on the charging capacitor 106a. The general-purpose input/output 108a (GPIO) may mediate communication between a microprocessor and the voltage control element 104a. For example, the inputs on the GPIO 108a may control the voltage control element 104a to open to isolate the charging capacitor 106a from the low voltage source 102 and to close to provide charge from the low voltage source 102 to the charging capacitor 106a.

A low voltage source 102 in direct and constant connection with an LED may not by itself supply the voltage required to power the LED. Therefore, rather than maintaining a constant connection between the low voltage source 102 and the LED 110, the voltage control element 104a may remain closed until the low voltage source 102 has charged the charging capacitor 106a to a predefined amount of voltage. When the charging capacitor 106a has been charged to the predefined amount, the voltage control element 104a may open while voltage control element 104b closes which may electrically isolate the low voltage source 102 from the charging capacitor 106a while electrically connecting the charging capacitor 106a to the LED 110. The isolation of the low voltage source 102 from the charging capacitor 106a may ensure there is no additional load on the low voltage power source 102 when the measurement circuit 107 is measuring light, thereby removing a source of noise. The voltage control element 104b may be controlled via a microprocessor to synchronize the opening of the voltage control element 104a with the closing of voltage control element 104b, and vice versa. The GPIO 108b may mediate communication between the microprocessor and the voltage control element 104b. Further, although the voltage control element 104b is located before the LED 110, it may alternatively be located after the LED 110.

A resistor may be connected in series with the LED 110 to control the current through the LED 110. Sufficient charge may thus flow from the charging capacitor 106a to the LED 110 to turn the LED on for a short time (i.e., cause the LED to emit light 112).

When the stored charge passes through the LED 110, the LED emits light 112. In an embodiment, the voltage control element 104b may be controlled by the microprocessor to provide charge from the charging capacitor 106a to the LED 110 for a period of time to cause the LED 110 to emit light 112 for a controlled duration of time, and after the period of time the voltage control element 104b may be controlled by the microprocessor to isolate the LED 110 from the charging capacitor 106a, thereby causing the LED 110 to cease emitting light. In this manner, light bursts may be generated from the LED 110 and the current draw of the circuit 100 may be minimized by only turning the LED 110 on for the period of time required to complete one measurement.

The light 112 emitted by the LED 110 propagates through a body part, such as an earlobe or a fingertip, and is measured by a receiver circuit 107 that includes a photodetector 114, such as a phototransistor or light sensor, that is coupled to an integrating capacitor 106b, and an analog-to-digital (A/D) converter 116. The photodetector 114 may be powered by a power supply 108c, such as the low power source 102, a regulated power supply, GPIO, or any other type power supply. The photodetector 114 converts the light 112 into a current and the integrating capacitor 106b stores this energy in the form of an electric field characterized by the voltage across the capacitor. The processor may measure the energy stored in the integrating capacitor 106b by connecting it to an analog to digital (A/D) converter 116 that converts the charge in the capacitor to a digital signal. The processor may use this digital signal to determine the amount of light that passed through the patient's tissues, and from that information, calculate a heart rate and/or blood oxygen reading. The processor may analyze the digital signal independently or in conjunction with other data points. Thus, the digital output of the A/D converter 116 may be the output of the receiver circuit 107 that may be analyzed by the processor as measurements of blood properties, such as measurements of the heart rate and/or blood oxygen level.

The processor, such as using the A/D converter 116, may be configured to discharge the integrating capacitor 106b just before a measurement is made in order to reduce a source of error in the measurements. This discharge of the integrating capacitor 106b may be synchronized with charging of the charging capacitor 106a and output of the light pulse of the LED 110 to improve the accuracy of measurements while reducing power requirements of the circuit 100.

Figure 2:
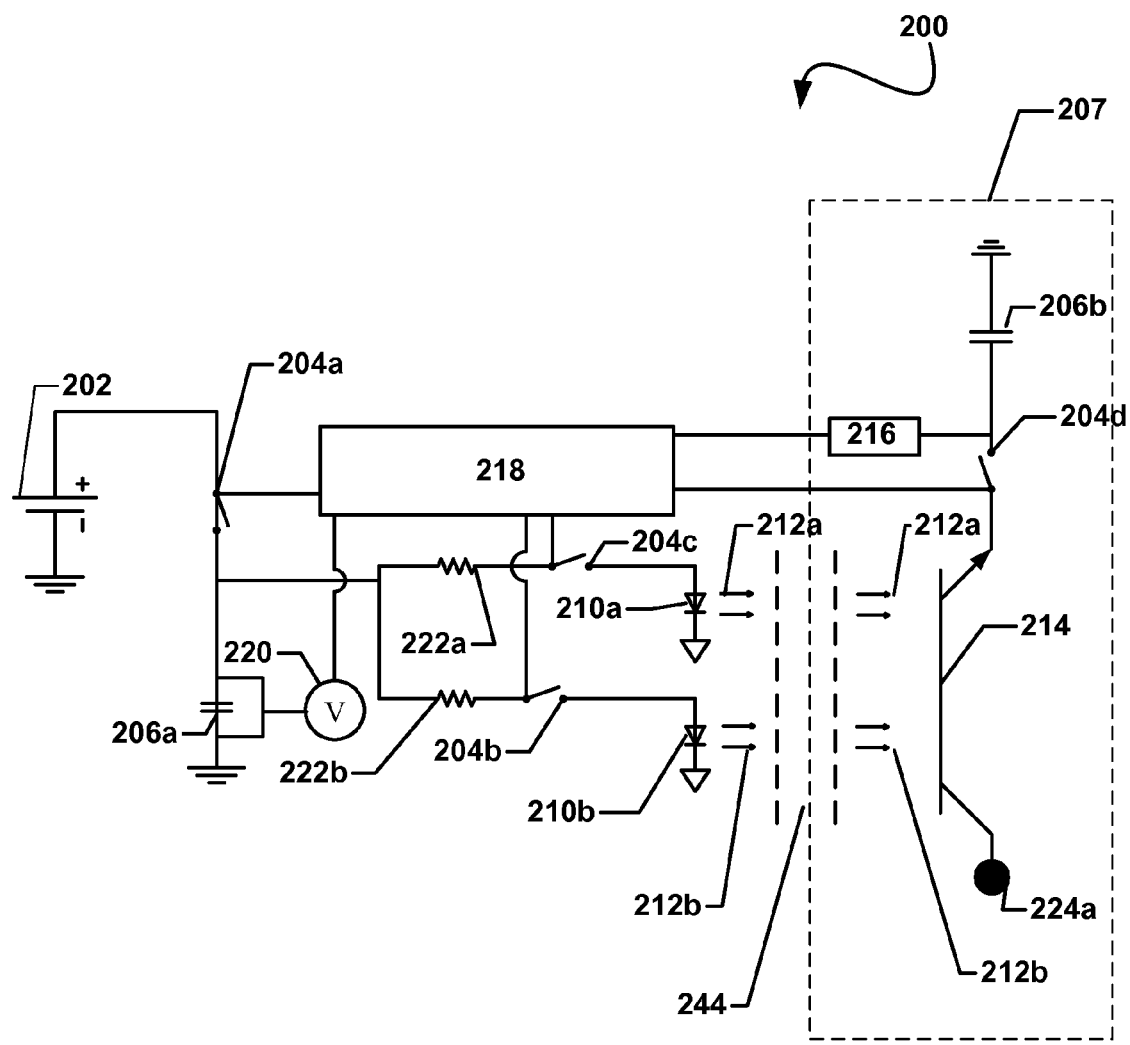
FIG. 2 is a circuit diagram illustrating a second embodiment circuit for device, such as a pulse oximeter or heart rate monitor, configured to minimize current draw.

FIG. 2 is a circuit diagram illustrating a second embodiment circuit 200 for a device (e.g., pulse oximeter or heart rate monitor) configured to minimize current draw. In an embodiment, the circuit 200 may be integrated into an electronic patch worn by a patient. A low voltage source 202 powers the charging capacitor 206a when the switch 204a is closed. The switch may be located anywhere on the loop containing the low voltage source 202 and switch 204a, provided it can electrically separate the low voltage source 202 and switch 204a. The microprocessor 218 may control when the switch 204a opens or closes. For example, the microprocessor 218 may close switch 204a to allow charging capacitor 206a to collect charge. The charge on the charging capacitor 206a may correspond via a known relationship to the voltage across the charging capacitor 206a. The voltage across the charging capacitor 206a may be monitored by the voltmeter 220. The voltmeter 220 may report the measured voltage to microprocessor 218.

When the voltage across charging capacitor 206a reaches a predetermined threshold, the microprocessor 218 may open switch 204a at an appropriate time and close switches 204b, 204c to allow charge to flow from charging capacitor 206a to red LED 210a and infrared LED 210b. The opening of switch 204a may disconnect the low charging capacitor 206a from the low voltage power source 202 to isolate the low voltage power source 202 from the charging capacitor 206a. In this manner, opening switch 204a may ensure there is no additional load on the low voltage power source 202 when a measurement of light is taking place, thereby removing a source of noise in the measurements. The switches 204b and 204c may be closed consecutively to measure different wavelength absorption rates in quick succession. Switches 204b, 204c may remain open while the capacitor is charging to prevent unnecessary drain on the low voltage source 202. Resistors 222a, 222b may be connected in series with a red LED 210a and an infrared LED 210b to control the current passing through each LED 210a, 210b. The resistors 222a, 222b may have the same or different resistances than each other. The resistors 222a, 222b may provide greater control on the allocation of current from the charging capacitor 206a, thus helping to eliminate the need for higher-current power supplies. In an embodiment, the switches 204b, 204c may be closed by the microprocessor 218 to provide charge from the charging capacitor 206a to the red LED 210a and infrared LED 210b for a period of time to cause the LEDs 210a and 210b to emit red light 212a and infrared light 212b, respectively. After the period of time, the switches 204b, 204c may be opened by the microprocessor 218 to isolate the LEDs 210a and 210b from the charging capacitor 206a to stop providing charge from the charging capacitor 206a to the LEDs 210a and 210b and stop the LEDs 210a and 210b from emitting red light 212a and infrared light 212b, respectively. In this manner, light bursts may be generated from the red LED 210a and the infrared LED 210b, and the current draw of the circuit 200 may be minimized by only turning the red LED 210a and infrared LED 210b on for the period of time. Additionally, only one LED 210a or 210b may be turned on at a time by closing either one of switch 204b or 204c, respectively, at a time. The charging capacitor 206a may need to be recharged to a known voltage before another LED 210a or 210b may be turned on.

When sufficient current passes through the red LED 210a and the infrared LED 210b, they emit red light 212a and infrared light 212b, respectively. The light 212a, 212b propagates through a body part 244, such as a fingertip or earlobe. The amount of light absorbed by the body part 244 may be a function of the amount of oxygen in the blood and the amount of blood in the body part 244 at the time of sampling. Specifically, a body part 244 with a relatively large amount of oxygen may tend to absorb more infrared light 212b and less red light 212a. A body part 244 with a relatively small amount of oxygen may tend to absorb less infrared light 212b and more red light 212a. After passing through the body part 244, the red light 212a and infrared light 212b may be absorbed by a photodetector 214, such as a phototransistor or a light sensor, of a receiver circuit 207 comprised of the photodetector 214, a switch 204d, a integrating capacitor 206b, and an A/D converter 216. Analysis of the absolute amplitude of the detected light signal as well as the relative amplitudes of the detected red light 212a and detected infrared light 212b may reveal various properties of the blood (i.e., blood properties), such as the pulse profile (e.g., heart rate) and the amount of oxygen in the blood.

The photodetector 214 may be powered by voltage source 224a. Microprocessor 218 may control switch 204d. When the switch 204d is open, current may not flow from the photodetector 214 and data may not be collected. When the switch 204d is closed, the photodetector 214 may transfer a charge onto the integrating capacitor 206b. The microprocessor may synchronize the opening and closing of switch 204d with switches 204a, 204b, 204c such that switch 204d is only closed when the photodetector 214 intercepts the light 212a, 212b. Power demand may be further reduced by leaving the switch 204d open when the photodetector is not receiving useful data. When the switch 204d is closed, current may flow from the photodetector 214 to the integrating capacitor 206b and be stored in the integrating capacitor 206b at the input to the A/D converter 216. The A/D converter 216 may measure the voltage at the integrating capacitor 206b and transfer the data to the microprocessor 218.

In an embodiment, the on periods of the red LED 210a and infrared LED 210b may be synchronized with the opening and closing of switch 204d by microprocessor 218. The microprocessor 218 may close the switch 204d to allow the photodetector 214 to start integrating its received signal just before the red LED 210a and infrared LED 210b are turned on by discharging the integrating capacitor 206b, and may control the A/D converter 216 to take a voltage measurement as soon as the red LED 210a and infrared LED 210b are off.

In an embodiment, the photodetector 214 may be a single device and may include two separate detectors tuned separately for each wavelength of light in use. In another embodiment, the photodetector 214 may be a single device with a broadband response that covers both red and IR portions of the spectrum. The digital output of the A/D converter 216 may be the output of the receiver circuit 207 that may be analyzed by the microprocessor 218 as measurements of the blood oxygen level.

Figure 3:
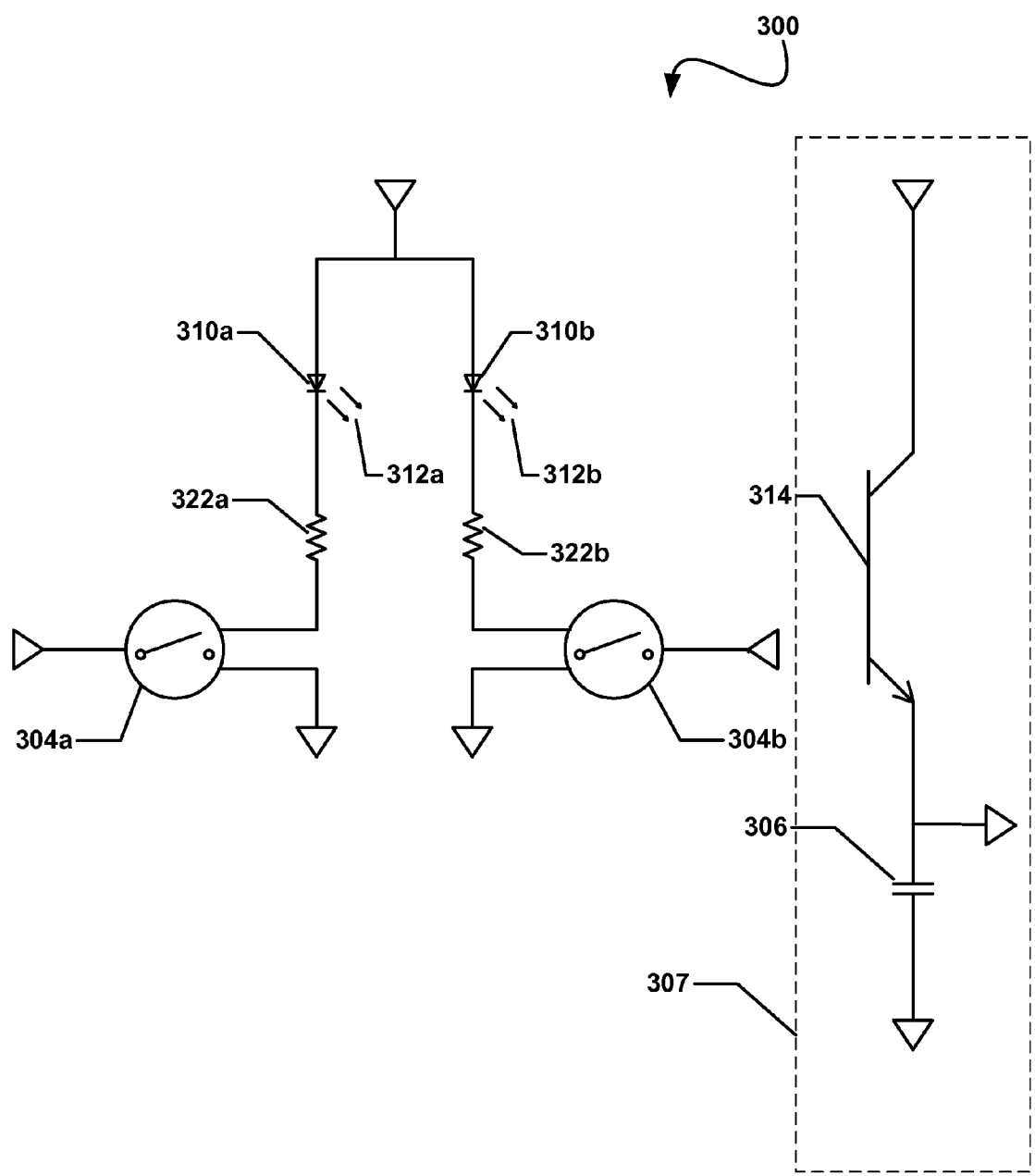
FIG. 3 is a circuit diagram illustrating a third embodiment circuit for device, such as a pulse oximeter or heart rate monitor, configured to minimize current draw.

FIG. 3 is a circuit diagram 300 illustrating a third embodiment circuit 300 for a device (e.g., pulse oximeter or heart rate monitor) configured to minimize current draw. In an embodiment, the circuit 300 may be integrated into an electronic patch worn by a patient. Switch 304a may control when current flows to LED 310a that emits red light 312a, and switch 304b may control when current flows to LED 310b that emits infrared light 312b. To minimize current draw, instead of remaining closed, the switches 304a, 304b may open and close at strategic times. Switches 304a, 304b may be controlled by the same or different microprocessors. Although LEDs 310a, 310b are connected in parallel in circuit diagram 300, in general they may also be powered by the same or different voltage sources. In an embodiment, the switches 304a, 304b may be closed by the microprocessor to provide charge to the LEDs 310a, 310b for a period of time to cause the LEDs 310a, 310b to emit light 312a and 312b, respectively. After the period of time, the switches 304a, and 304b may be opened by the microprocessor to isolate the LEDs 310a, 310b to stop providing charge to the LEDs 310a, 310b and stop the LEDs 310a, 310b from emitting light, respectively. In this manner, light bursts may be generated from the LEDs 310a, 310b and the current draw of the circuit 300 may be minimized by only turning the LEDs 310a, 310b on for the period of time.

Resistor 322a may control the amount of current that flows to LED 310a. Resistor 322a may thus control the amplitude of red light 312a emitted from LED 310a. Resistor 322b may control the amount of current that flows to LED 310b. Resistor 322b may thus control the amplitude of infrared light 312b emitted from LED 310b. The resistors 322a, 322b may have the same or different resistances, and may have fixed or variable resistance. Additionally, although LEDs 310a, 310b emit red and infrared light 310a, 310b, respectively, in general circuit diagram 300 may include LEDs that emit light in any portion of the electromagnetic spectrum.

Circuit 300 may include a receiver circuit 307 that includes a phototransistor 314 and a integrating capacitor 306. The phototransistor 314 may detect red light 312a and infrared light 312b and convert the red light 312a and infrared light 312b to electrical energy. The electrical energy generated by the phototransistor 314 may be stored in an integrating capacitor 306. A resulting charge may collect on integrating capacitor 306, creating a voltage over the integrating capacitor 306. The analog voltage signal may be measured, converted to a digital signal, and analyzed. Persons skilled in the art will appreciate that the phototransistor 314 may be substituted for any device capable of converting photons to a current. Further, to minimize current draw, rather than remaining on continuously, the phototransistor 314 may only turn on when the LEDs 310a, 310b emit light 312a, 312b.

While the circuits 200 and 300 illustrated in FIGS. 2 and 3, respectively, each include two LEDs 210a, 210b and 310a, 310b, respectively, in embodiments in which the circuits 200 and 300 are used only to measure heart rate information (i.e., operated as a heart rate monitor), only one of the two LEDs may be needed. The second LED may be removed from the circuit, or may merely remain off, when heart rate information is the only blood property to be measured.

Figure 4:
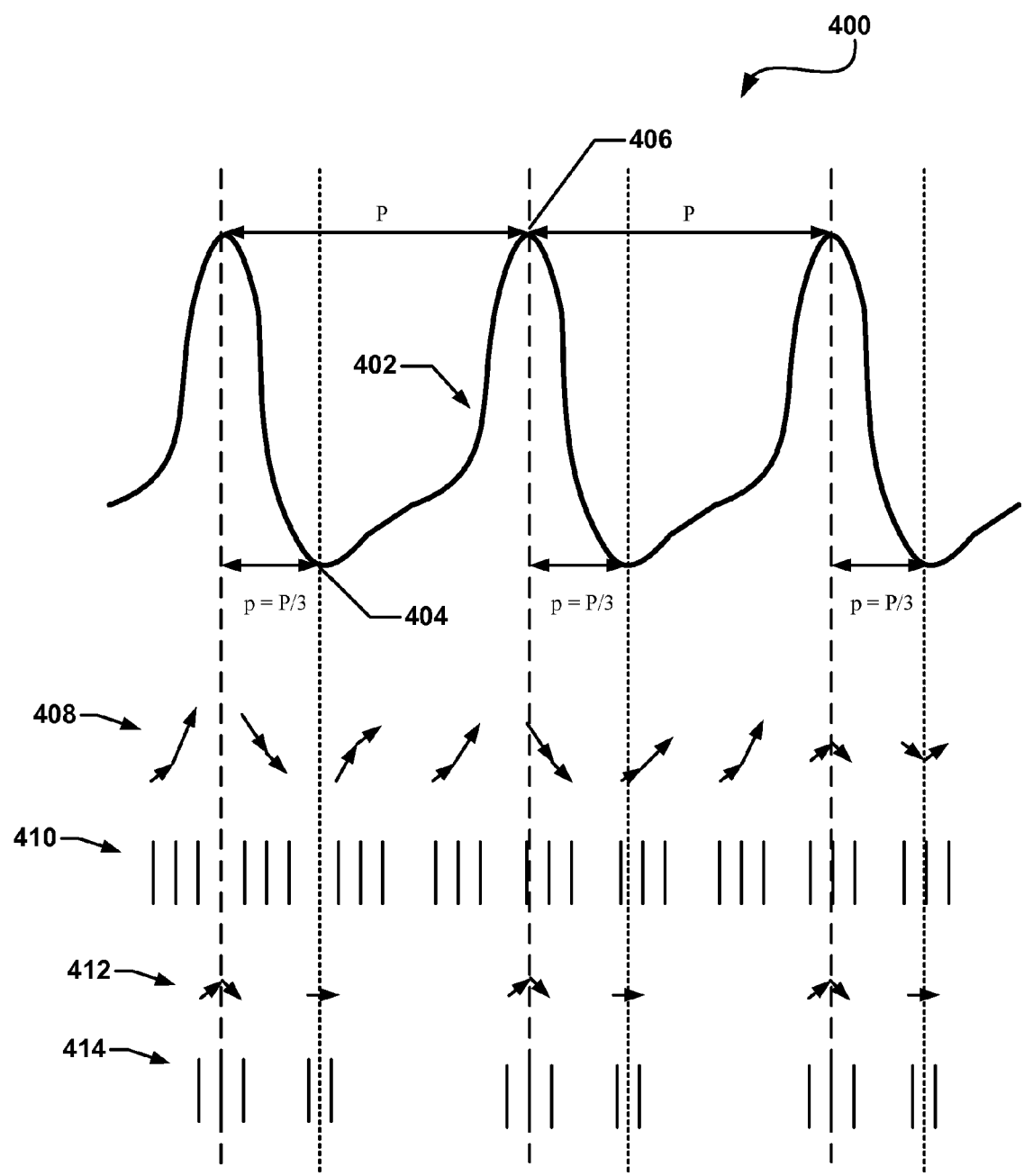
FIG. 4 is a sample heart rate graph illustrating a lock-in procedure and subsequent pulse measurements.

FIG. 4 is a sample heart rate graph 400 illustrating an embodiment lock-in procedure and subsequent pulse measurements. Waveform 402 has a pulse period of P such that each pulse maximum 406 occurs once every P units of time. As is typical, the pulse minima 404 occur p=P/3 units of time after the pulse maxima 406.

At various times, such as when it begins monitoring oxygen levels, the pulse oximeter may need to lock on to waveform 402. As used herein, to be locked on to waveform 402 means to be able to predict the curve of a subsequent portion of the waveform 402 to within some error. Rather than continuously sampling waveform 402, the pulse oximeter may instead sample the waveform 402 periodically to minimize current draw. The ticks 410 represent when the pulse oximeter samples data (ex., when charging integrating capacitor 206b (FIG. 2) discharges, causing LEDs 210a, 210b (FIG. 2) to emit light 212a, 212b (FIG. 2)) before it is locked on to waveform 402. Sampling occurs only during an individual tick 410. Persons skilled in the art will appreciate that although ticks 410 occur in groups of three in FIG. 4, the ticks may also sample in groups of any number, such as two. The number of ticks 410 in a group may also vary, such as alternating between two and three ticks per group.

A point on the waveform 402 may be measured and analyzed at each tick 410. In an embodiment, the slope 408 between the ticks 410 in each group may be calculated. The pulse maxima 406 and pulse minima 404 are located where the slope is zero on the waveform 402. Thus, as more data is collected and analyzed, the pulse maxima 406 and pulse minima 404 become more predictable. As various points on the waveform are sampled, the time between the samples (frequency) and the offset of the samples may be varied until the pulse oximeter has locked onto the pulse maxima 406 and pulse minima 404. Both the slope 408 of the waveform 402 and the difference between the minimum and maximum readings may be used to locate the pulse maxima 406 and pulse minima 404. Any algorithm may be used to locate the pulse maxima 406 and pulse minima 404, such as the MM algorithm. That the pulse minima 404 usually occur one-third of a period after the pulse maxima 406 may also be used in locating the maxima 406 and minima 404.

One potential issue when locking on to waveform 402 may be the possibility of locking onto a false waveform that is actually a fraction of the period of the true waveform. For example, assume the period of a waveform is 120 beats/minute. If the sampling begins at 50 samples per minute, the sampling rate will increase as it searches for the waveform period. However, the samples may lock on to a "false" period of 60 beats/minute, thereby only collecting data for alternating pulse extremes. To avoid this potential issue, the sampling may begin at a high rate, such as 180 samples per minute, and decrease as it locks on to the true period of the waveform, such as period P of waveform 402.

After the pulse oximeter has locked onto the pulse maxima 406 and pulse minima 404, the frequency of the samples may decrease even further, as illustrated by ticks 414. Data may continue to be sampled and analyzed to ensure the pulse oximeter remains locked on, for example by measuring the slopes 412 of the waveform 402 between the samples. For example, for groups of three or more, the slope may be analyzed to ensure that the zero of the slope falls within the group of samples. For groups of two, the slope may be analyzed to ensure that it is close to zero. As shown in FIG. 4, a group of three samples may encompass pulse maxima 406 and a group of two samples may encompass pulse minima 404. However, groups consisting of any number of samples may be used. For example, groups of two may encompass the pulse maxima 406 and groups of three may encompass pulse minima 404, or the number of samples in groups may vary, such as between two, three, four, etc. By limiting the number and frequency of samples, current consumption may be minimized. To further minimize current draw, samples may not be taken for every maxima and minima. For example, if the pulse oximeter is not monitoring an irregular heartbeat, the pulse oximeter may only sample one out of every three or five (or other fraction) periods.

Figure 5A:
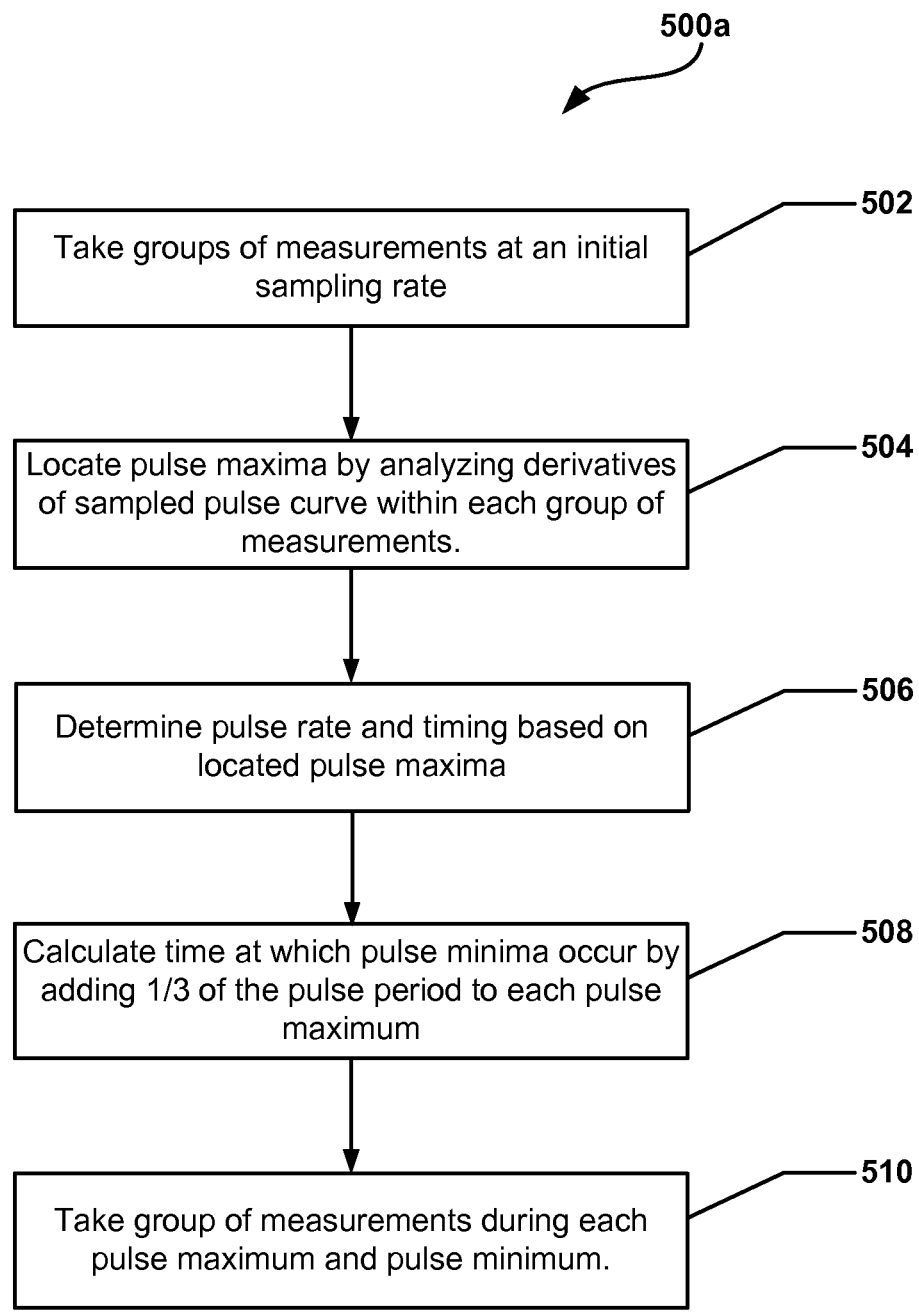
FIG. 5A is a process flow diagram illustrating an embodiment method for executing a lock-in procedure.

FIG. 5A is a process flow diagram illustrating an embodiment method 500a to lock on to the waveform. In an embodiment, the operations of the method 500a may be performed by a processor of a device (e.g., pulse oximeter), such as the microprocessor 218 described above. In block 502 the processor of the pulse oximeter may control the pulse oximeter circuitry, such as circuit elements 104a, 104b, 116 (FIG. 1), 204a, 204b, 204c, 204d, 216 (FIG. 2), 304a, 304b (FIG. 3) described above, to take groups of measurements at an initial sampling rate. This initial sampling rate may be relatively high, such as 180 samples per minute or that for a 90 Hz pulse rate. In an embodiment, the sampling rate may be selected such that a full set of readings is not taken over one pulse cycle, thereby drawing less power from a coin cell battery or printed cell battery compared to taking a full set of readings over one pulse cycle. In block 504, the processor of the pulse oximeter may locate pulse maxima by analyzing the derivatives of the sampled pulse curve within each group of measurements. In block 506 the processor of the pulse oximeter may determine the pulse rate (e.g., heart rate) and timing based on the located pulse maxima. In block 508 the processor of the pulse oximeter may calculate the time at which pulse minima occur by adding one-third of the pulse period to each pulse maximum. In block 510 the pulse oximeter processor may control the pulse oximeter circuitry, such as circuit elements 104a, 104b, 116 (FIG. 1), 204a, 204b, 204c, 204d, 216 (FIG. 2), 304a, 304b (FIG. 3) described above, to take a group of measurements during each pulse maximum and pulse minimum. The frequency of these groups of measurements may be less frequent than the initial sampling rate to avoid excessive current draw.

Figure 5B:
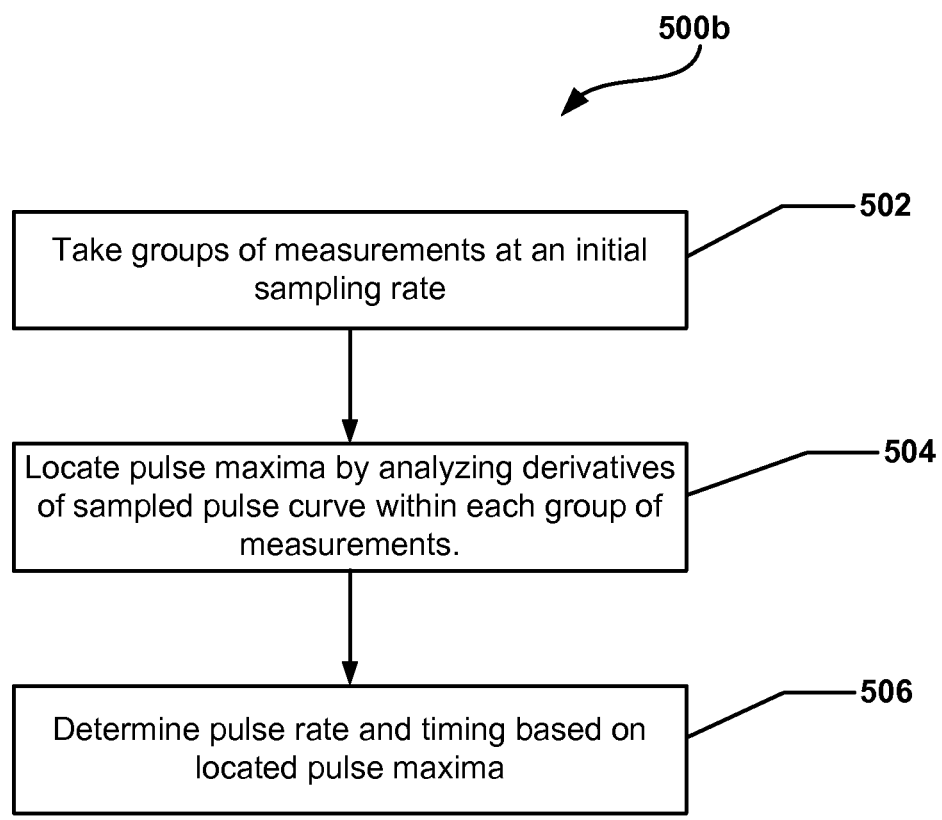
FIG. 5B is a process flow diagram illustrating an embodiment method for determining a heart rate based on an amount of light received by a heart rate monitor.

FIG. 5B is a process flow diagram illustrating an embodiment method 500B to determine a heart rate based on the amount of light received by a heart rate monitor. In an embodiment, the operations of the method 500b may be performed by a processor of a device (e.g., heart rate monitor or a pulse oximeter operating in a heart rate monitor mode), such as the microprocessor 218 described above. In block 502, the processor of the heart rate monitor may control the heart rate monitor circuitry, such as circuit elements 104a, 104b, 116 (FIG. 1), 204a, 204b, 204c, 204d, 216 (FIG. 2), 304a, 304b (FIG. 3) described above, to take groups of measurements at an initial sampling rate. This initial sampling rate may be relatively high, such as 180 samples per minute for a 90 Hz pulse rate. In an embodiment, the sampling rate may be selected such that a full set of readings is not taken over one pulse cycle, thereby drawing less power from a coin cell battery or printed cell battery compared to taking a full set of readings over one pulse cycle. In an embodiment, because only the heart rate may be of interest to a heart rate monitor, or a pulse oximeter operating in a heart rate monitor mode, only one LED of the heart rate monitor circuitry may be turned on to take the groups of measurements. In block 504, the processor of the heart rate monitor may locate pulse maxima by analyzing the derivatives of the sampled pulse curve within each group of measurements. In block 506 the processor of the heart rate monitor may determine the pulse rate (e.g., heart rate) and timing based on the located pulse maxima.

Figure 6:
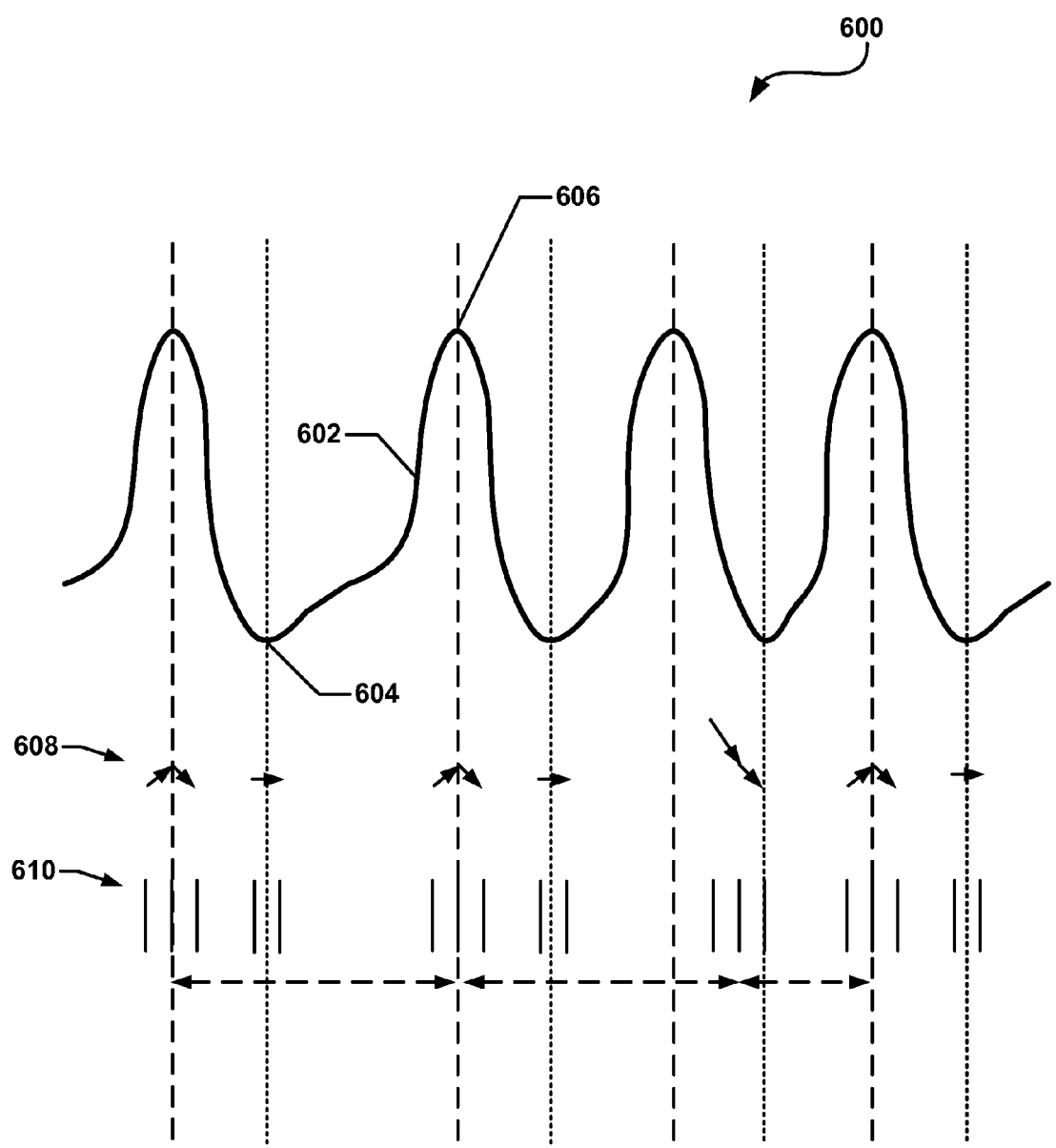
FIG. 6 is a sample heart rate graph illustrating a sample rate adjustment according to an embodiment.

FIG. 6 is a sample heart rate graph 600 illustrating a sample rate adjustment according to an embodiment. Four periods of waveform 602 are shown. After the two leftmost periods, the frequency of pulse maxima 606 and pulse minima 604 increases, corresponding to an increasing heart rate. In this graph 600, the pulse oximeter may already be locked on to the waveform 602 and may be taking periodic samples, the timing of which is illustrated by ticks 610. Because the pulse oximeter may already be locked on, a group of samples encompasses the pulse maxima 606 in the two leftmost periods and the pulse minima 604 in the two leftmost periods. To ensure that the pulse oximeter remains locked on to the waveform 602, the slopes 608 of the waveform 602 between the samples are analyzed.

Notwithstanding the increase in heart rate after the two leftmost periods, the pulse oximeter may sample when the subsequent pulse maximum is predicted to occur based upon its previous measurements. After analyzing the data and noting that the slope 608 is negative, the sampling may return to a pre-lock on mode, and perform operations as described above with reference to FIG. 4. This may include a change in group sample size, a change in sample frequency, a change in group sample frequency, and changes in any other suitable factors regarding sampling.

FIG. 6 illustrates three samples contained within the group that does not encompass a pulse maximum 606, although the group could generally include any number of samples. The horizontal dashed arrows below the ticks 610 illustrate that the group sample frequency may change when the slope is measured to be negative after the pulse oximeter is already locked on. FIG. 6 shows group frequency increase; however, group frequency may alternatively decrease after detecting a change in heart rate.

FIG. 6 illustrates the pulse oximeter quickly locking back on to the waveform 602 after just one group measurement. In general, it may take more than one group measurement to lock back on to a heart rate after it has increased. Many group measurements may be required, similar to the samples illustrated by ticks 410 in FIG. 4. Using sporadic sampling rather than continuous sampling to lock back on to the waveform 602 decreases power consumption, thereby enabling use of a low voltage battery or the equivalent.

Figure 7:
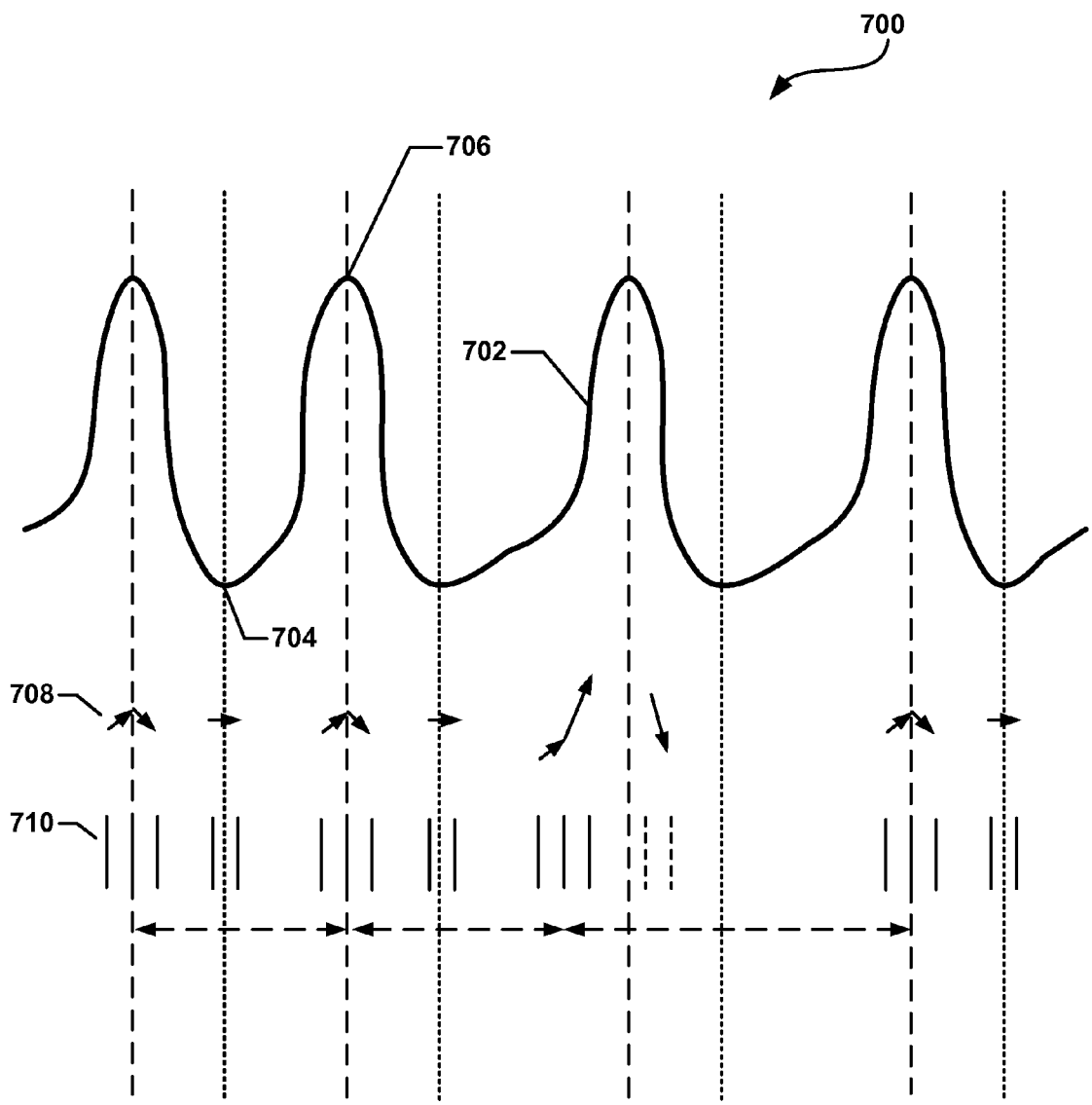
FIG. 7 is sample heart rate graph illustrating another sample rate adjustment according to an embodiment.

FIG. 7 is sample heart rate graph 700 illustrating another sample rate adjustment according to an embodiment. In this graph 700, the frequency of pulse maxima 706 and pulse minima 704 decreases, corresponding to an decreasing heart rate. In this graph 700, as in graph 600 illustrated in FIG. 6, the pulse oximeter may already be locked on to the waveform 702 and may be taking periodic samples, the timing of which is illustrated by ticks 710. Because it is already locked on, a group of samples encompasses the pulse maxima 706 in the two leftmost periods and the pulse minima 704 in the two leftmost periods. To ensure that the pulse oximeter remains locked on to the waveform 702, the slopes 708 of the waveform 702 between the samples are analyzed.

Notwithstanding the decrease in heart rate after the two leftmost periods, the pulse oximeter may sample when the subsequent pulse maximum is predicted to occur based upon its previous measurements. After analyzing the data and noting that the slope 708 is positive, the sampling may return to pre-lock on mode, as described above with reference to FIG. 4. This may include a change in group sample size, a change in sample frequency, a change in group sample frequency, and changes in any other suitable factors regarding sampling.

FIG. 7 illustrates three samples contained within the group that does not contain a pulse maximum 706, although the group could generally include any number of samples. The pulse oximeter may or may not sample for the pulse minimum 704 after measuring a positive slope where the pulse maximum 706 is predicted to be. This is illustrated by the two dashed vertical ticks 710. The subsequent group measurements, including a subsequent sample for the pulse minimum 706, may be any number of measurements, regardless of previous group measurements. For example, the subsequent sample for a pulse minimum 706 could be three or more measurements. The horizontal dashed arrows below the ticks 710 illustrate that the group sample frequency may change when the slope is measured to be positive after the pulse oximeter is already locked on. FIG. 7 shows group frequency decrease; however, group frequency may alternatively increase after detecting a change in heart rate.

FIG. 7 illustrates the pulse oximeter quickly locking back on to the waveform 702 after just one group measurement. In general, it may take more than one group measurement to lock back on to a heart rate after it has increased. Many group measurements may be required, similar to the samples illustrated by ticks 410 in FIG. 4. Using sporadic sampling rather than continuous sampling to lock back on to the waveform 702 decreases power consumption, thereby enabling use of a low voltage battery or the equivalent.

Figure 8:
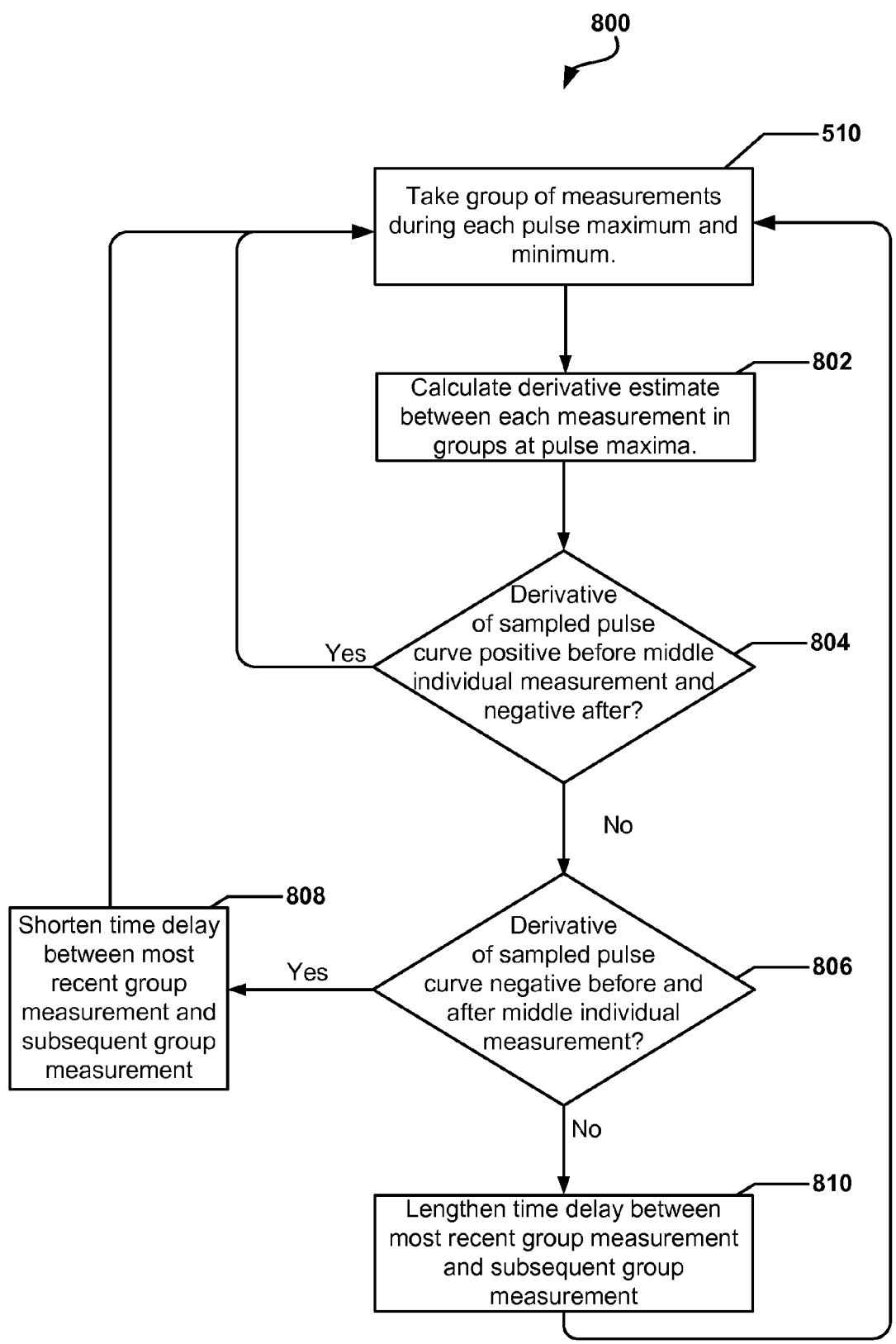
FIG. 8 is a process flow diagram illustrating an embodiment sample rate adjustment procedure.

FIG. 8 is a process flow diagram illustrating an embodiment method 800 for sample timing adjustment. In an embodiment, the operations of method 800 may be performed by a processor of a device (e.g., a pulse oximeter), such as microprocessor 218 described above. The operations of method 800 may be performed in conjunction with the operations of method 500 described above, for example when the processor of the pulse oximeter locks on to the pulse maxima and minima but the heart rate changes and the processor of the pulse oximeter has to re-locate the pulse maxima and minima. As described above, in block 510 the pulse oximeter processor may control the pulse oximeter circuitry, such as circuit elements 104a, 104b, 116 (FIG. 1), 204a, 204b, 204c, 204d, 216 (FIG. 2), 304a, 304b (FIG. 3) described above, to take a group of measurements during each pulse maximum and pulse minimum. In block 802 the processor of the pulse oximeter may calculate the derivative estimate between each measurement in the groups at the pulse maxima. In block 804 the processor may determine whether the derivative of the sampled pulse curve is positive before the middle individual measurement and negative after. In response to determining the sampled pulse curve is positive before the middle individual measurements and negative after (i.e., determination block 804="Yes"), then no adjustment may be necessary and in block 510 the processor may continue to take subsequent groups of measurements during each pulse maximum and minimum.

In response to determining that the derivative of the sampled pulse curve is not positive before the middle individual measurement and negative after (i.e., determination block 804="No"), in determination block 806 the processor of the pulse oximeter may analyze whether the derivative of the sampled pulse curve is negative both before and after the middle individual measurement 806. In response to determining the derivative of the sampled pulse curve is negative both before and after the middle individual measurement (i.e., determination block 806="Yes"), in block 808 the processor of the pulse oximeter may shorten the time delay between the most recent group measurement and the subsequent group measurement. In block 510 the pulse oximeter may again take groups of measurements during each pulse maximum and minimum.

In response to determining that the derivative of the sampled pulse curve is positive both before and after the middle individual measurement (i.e., determination block 806="No"), in block 810 the processor of the pulse oximeter may lengthen the time delay between the most recent group measurement and subsequent group measurement. In block 510 the pulse oximeter may again take groups of measurements during each pulse maximum and minimum.

Figure 9:
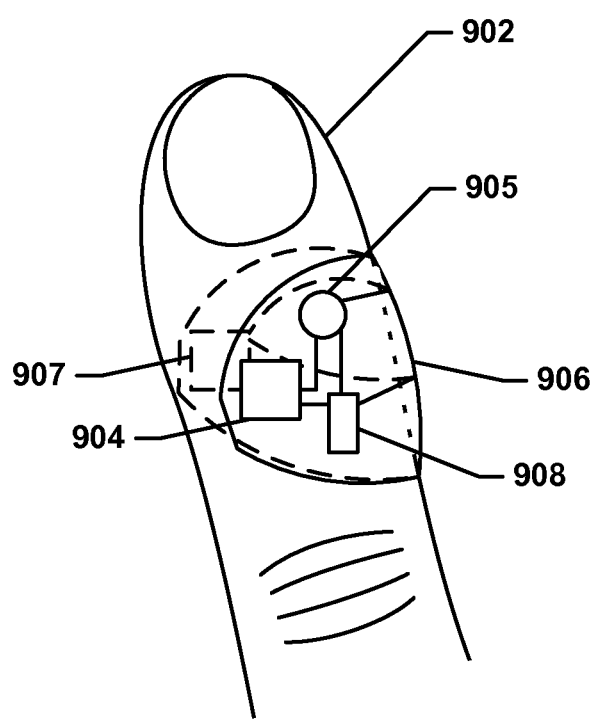
FIG. 9 is a diagram illustrating an embodiment electronic patch including a pulse oximeter or heart rate monitor placed on a patient.

FIG. 9 illustrates an embodiment electronic patch 906 including a pulse oximeter or heart rate monitor placed on a patient 902, such as on a skin surface of a finger of a patient 902. In various embodiments, an electronic patch 906 may be flexible and resilient so that placement and removal of the electronic patch 906 from the patient 902 does not damage the electronic patch 906. The electronic patch 902 may include a pulse oximeter or heart rate monitor circuit comprised of a transmitting circuit 904 comprised of at least one LED, a capacitor, and a low voltage power source, such as a coin cell battery or printed cell battery, a receiver circuit 907 configured to measure light emitted by the at least one LED, and a processor 908 connected to the transmitting circuit 904 and receiver circuit 907. As specific examples, the pulse oximeter or heart rate monitor circuit may be the circuit 100, 200, or 300 described above. An adhesive layer may affix the electronic patch 906 to the patient 902.

Further, those of skill in the art will appreciate that the foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope embodiments.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A device, comprising:
a capacitor configured to be charged by a low voltage power source;
at least one light-emitting diode (LED) connected to the capacitor by a switch;
a receiver circuit configured to measure light emitted by the at least one LED after the light passes through tissue of a patient, wherein the receiver circuit comprises a first photodetector; and
a processor connected to the switch and the receiver circuit, wherein the processor is configured with processor executable instructions to perform operations comprising:
determining a time of a pulse maxima and a time of a pulse minima based on measurements of light received by the first photodetector of the receiver circuit;
determining a derivative estimate of a sampled pulse curve of a group of pulse measurements taken at the determined time of the pulse maxima, wherein the group of pulse measurements are based on the measurements of light received by the first photodetector of the receiver circuit;
adjusting a time delay between the determined time of the pulse maxima and the determined time of the pulse minima based on the determined derivative estimate of the sampled pulse curve of the group of pulse measurements taken at the determined time of the pulse maxima;
controlling the switch to provide charge from the capacitor to the at least one LED to cause the at least one LED to emit light at the expiration of the adjusted time delay;
controlling the switch to isolate the capacitor from the at least one LED to cause the at least one LED to stop emitting light after a period of time;
measuring an amount of light received by the receiver circuit after the period of time; and
determining a blood property based at least in part on the measurement of the amount of light received by the receiver circuit after the period of time.

2. The device of claim 1, wherein the processor is configured with processor-executable instructions to perform operations such that determining the blood property based at least in part on the measurement of the amount of light received by the receiver circuit after the period of time comprises determining a heart rate based at least in part on the measurement of the amount of light received by the receiver circuit after the period of time.

3. The device of claim 1, wherein the processor is configured with processor-executable instructions to perform operations such that determining the blood property based at least in part on the measurement of the amount of light received by the receiver circuit after the period of time comprises determining a blood oxygen level based at least in part on the measurement of the amount of light received by the receiver circuit after the period of time.

4. The device of claim 3, wherein the processor is configured with processor-executable instructions to perform operations further comprising:
determining when the capacitor is charged by the low voltage power source to a predetermined voltage; and
controlling the switch to provide charge from the capacitor to the at least one LED to cause the at least one LED to emit light in response to determining the capacitor is charged by the low voltage power source to a predetermined voltage.

5. The device of claim 3, wherein the processor is configured with processor executable instructions to perform operations such that:
determining the blood oxygen level based at least in part on the measured amount of light received by the receiver circuit after the period of time comprises determining a blood oxygen level and a pulse waveform measurement based at least in part on the measured amount of light received by the receiver circuit after the period of time.

6. The device of claim 5, wherein the processor is configured with processor executable instructions to perform operations such that determining the time of the pulse maxima and the time of the pulse minima based on measurements of light received by the first photodetector of the receiver circuit comprises:
determining a local maxima of a sampled pulse curve of the group of pulse measurements based upon a derivative estimate of the sampled pulse curve;
determining a pulse rate and timing based on the determined local maxima of the sampled pulse curve of the group of pulse measurements; and
determining the time of the pulse maxima and the time of the pulse minima based on the determined pulse rate and timing and the determined local maxima.

7. The device of claim 3, wherein the at least one LED is two different LEDs, and wherein the two different LEDs each emit light of different wavelengths.

8. The device of claim 7, wherein the two LEDs comprise one red LED and one infrared LED.

9. The device of claim 1, wherein the low voltage source is a coin cell battery or a printed cell battery.

10. A method of measuring a blood property of a patient, comprising:
determining a time of a pulse maxima and a time of a pulse minima based on measurements of light received by a first photodetector of a receiver circuit;
determining a derivative estimate of a sampled pulse curve of a group of pulse measurements taken at the determined time of the pulse maxima, wherein the group of pulse measurements are based on the measurements of light received by the first photodetector of the receiver circuit;
adjusting a time delay between the determined time of the pulse maxima and the determined time of the pulse minima based on the determined derivative estimate of the sampled pulse curve of the group of pulse measurements taken at the determined time of the pulse maxima;
charging a capacitor with a low voltage power source;
connecting the capacitor to a light-emitting diode (LED) positioned to transmit light into tissue of the patient at the expiration of the adjusted time delay;
isolating the capacitor from the LED to cause the LED to stop emitting light after a period of time;
measuring an amount of light passing through the tissue of the patient received by the receiver circuit after the period of time; and
determining a blood property based at least in part on the measurement of the amount of light after the period of time.

11. The method of claim 10, wherein determining a blood property based at least in part on the measurement of the amount of light after the period of time comprises determining a heart rate based at least in part on the measurement of the amount of light after the period of time.

12. The method of claim 10, wherein determining the blood property based at least in part on the measurement of the amount of light after the period of time comprises determining a blood oxygen level based at least in part on the measurement of the amount of light after the period of time.

13. The method of claim 12, further comprising:
determining when the capacitor is charged by the low voltage power source to a predetermined voltage;
disconnecting the capacitor from the low voltage power source in response to determining that the capacitor is charged by the low voltage power source to a predetermined voltage; and
connecting the capacitor to a light-emitting diode (LED) positioned to transmit light into tissue of the patient in response to determining the capacitor is charged by the low voltage power source to a predetermined voltage.

14. The method of claim 13, wherein:
determining the blood oxygen level based at least in part on the measurement of the amount of light after the period of time comprises determining a blood oxygen level and a pulse waveform measurement based at least in part on the measurement of the amount of light after the period of time.

15. The method of claim 14, wherein determining the time of the pulse maxima and the time of the pulse minima based on measurements of light received by the first photodetector of the receiver circuit comprises:
determining a local maxima of a sampled pulse curve of the group of pulse measurements based upon a derivative estimate of the sampled pulse curve;
determining a pulse rate and timing based on the determined local maxima of the sampled pulse curve of the group of pulse measurements; and
determining the time of the pulse maxima and the time of a pulse minima based on the determined pulse rate and timing and the determined local maxima.

16. The method of claim 10, wherein the low voltage source is a coin cell battery or a printed cell battery.

17. A device, comprising:
means for determining a time of a pulse maxima and a time of a pulse minima based on measurements of light received by a first photodetector of a receiver circuit;
means for determining a derivative estimate of a sampled pulse curve of a group of pulse measurements taken at the determined time of the pulse maxima, wherein the group of pulse measurements are based on the measurements of light received by the first photodetector of the receiver circuit;
means for adjusting a time delay between the determined time of the pulse maxima and the determined time of the pulse minima based on the determined derivative estimate of the sampled pulse curve of the group of pulse measurements taken at the determined time of the pulse maxima;
means for charging a capacitor with a low voltage power source;
means for connecting the capacitor to a light-emitting diode (LED) positioned to transmit light into tissue of a patient at the expiration of the adjusted time delay;
means for isolating the capacitor from the LED to cause the LED to stop emitting light after a period of time;
means for measuring an amount of light passing through the tissue of the patient received by the receiver circuit after the period of time; and means for determining a blood property based at least in part on the measurement of the amount of light after the period of time.

18. The device of claim 17, wherein means for determining the blood property based at least in part on the measurement of the amount of light after the period of time comprises means for determining a heart rate based at least in part on the measurement of the amount of light after the period of time.

19. The device of claim 17, wherein means for determining the blood property based at least in part on the measurement of the amount of light after the period of time comprises means for determining a blood oxygen level based at least in part on the measurement of the amount of light after the period of time.

20. The device of claim 19, further comprising:
means for determining when the capacitor is charged by the low voltage power source to a predetermined voltage; and
means for connecting the capacitor to a light-emitting diode (LED) positioned to transmit light into tissue of the patient in response to determining the capacitor is charged by the low voltage power source to a predetermined voltage.

21. The device of claim 20, wherein:
means for determining the blood oxygen level based at least in part on the measurement of the amount of light after the period of time comprises means for determining a blood oxygen level and a pulse waveform measurement based at least in part on the measurement of the amount of light after the period of time.

22. The device of claim 21, wherein means for determining the time of the pulse maxima and the time of the pulse minima based on measurements of light received by the first photodetector of the receiver circuit comprises:
means for determining a local maxima of a sampled pulse curve of the group of pulse measurements based upon a derivative estimate of the sampled pulse curve;
means for determining a pulse rate and timing based on the determined local maxima of the sampled pulse curve of the group of pulse measurements; and
means for determining the time of the pulse maxima and the time of a pulse minima based on the determined pulse rate and timing and the determined local maxima.

23. The device of claim 17, wherein the low voltage source is a coin cell battery or a printed cell battery.

24. A non-transitory processor readable medium having stored thereon processor executable instructions configured to cause a processor to perform operations, comprising:
determining a time of a pulse maxima and a time of a pulse minima based on measurements of light received by a first photodetector of a receiver circuit;
determining a derivative estimate of a sampled pulse curve of a group of pulse measurements taken at the determined time of the pulse maxima, wherein the group of pulse measurements are based on the measurements of light received by the first photodetector of the receiver circuit;
adjusting a time delay between the determined time of the pulse maxima and the determined time of the pulse minima based on the determined derivative estimate of the sampled pulse curve of the group of pulse measurements taken at the determined time of the pulse maxima;
charging a capacitor with a low voltage power source;
connecting the capacitor to a light-emitting diode (LED) positioned to transmit light into tissue of a patient at the expiration of the adjusted time delay;
isolating the capacitor from the LED to cause the LED to stop emitting light after a period of time;
measuring an amount of light passing through the tissue of the patient received by the receiver circuit after the period of time; and
determining a blood property based at least in part on the measurement of the amount of light after the period of time.

* * * * *